United States Patent [19]

Hayes

[11] Patent Number: 4,776,983
[45] Date of Patent: Oct. 11, 1988

[54] POLYMERIZATION OF FATTY ACIDS

[75] Inventor: Kathryn S. Hayes, Norristown, Pa.

[73] Assignee: Union Camp Corporation, Wayne, N.J.

[21] Appl. No.: 714,997

[22] Filed: Mar. 22, 1985

[51] Int. Cl.$^4$ .............................................. C08H 3/00
[52] U.S. Cl. .................................................. 260/407
[58] Field of Search ........................................ 260/407

[56] References Cited

U.S. PATENT DOCUMENTS

| | | | |
|---|---|---|---|
| 2,793,219 | 5/1957 | Barrett et al. | 260/407 |
| 2,955,121 | 10/1960 | Myer et al. | 260/407 |
| 3,632,822 | 1/1972 | Conroy | 260/407 |

FOREIGN PATENT DOCUMENTS 6406153  6/1964  Netherlands ...................... 260/407

Primary Examiner—Charles F. Warren
Assistant Examiner—Elizabeth A. Hanley
Attorney, Agent, or Firm—Edward J. Sites

[57] ABSTRACT

A process for polymerizing unsaturated fatty acids comprises heating the fatty acids in the presence of a catalytic proportion of an unactivated clay and water. The product polymerizate is distilled to separate unreacted monomer acids which are separately polymerized under similar conditions. Higher overall polymer yields are obtained.

10 Claims, 1 Drawing Sheet

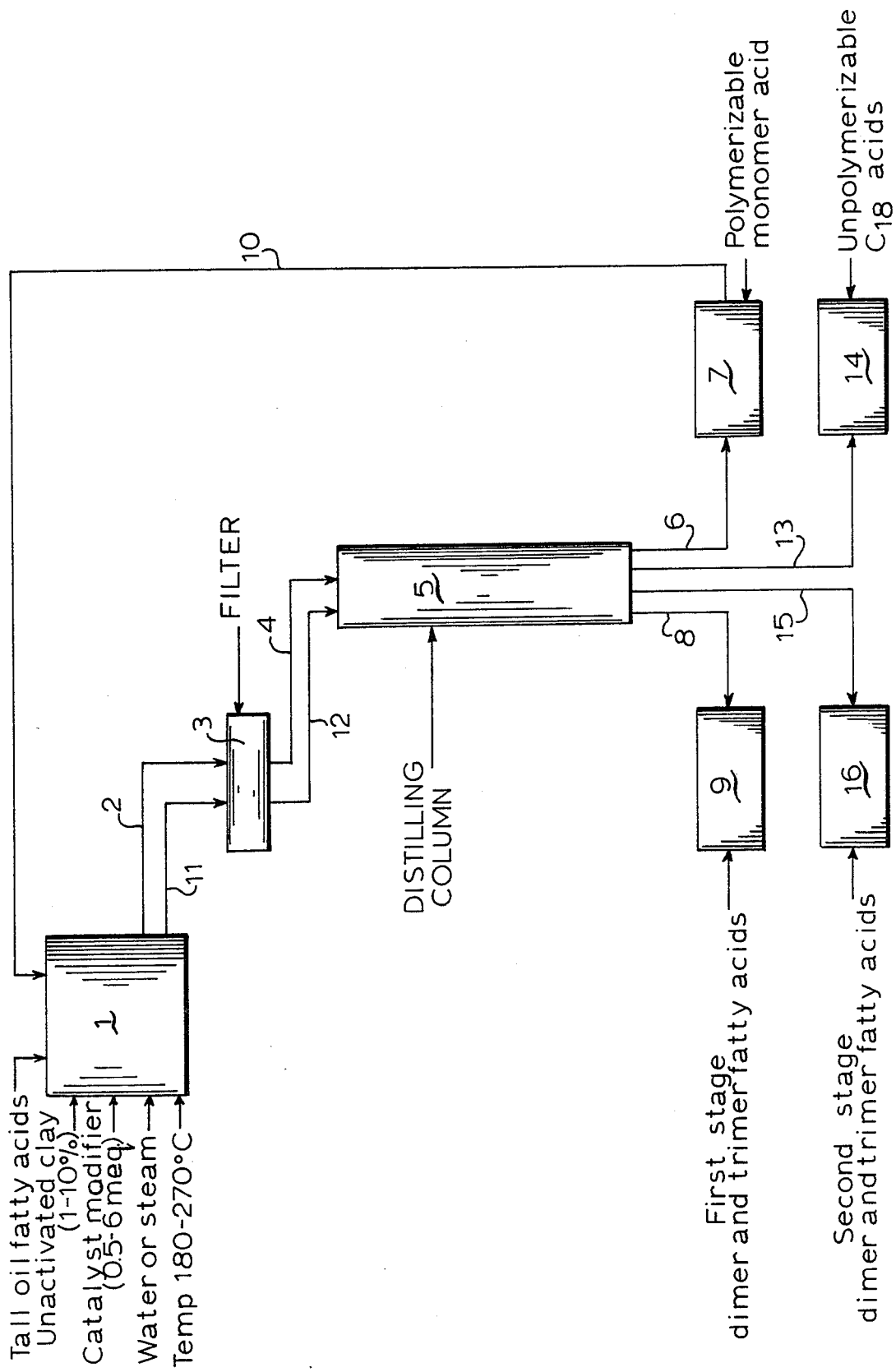

4,776,983

POLYMERIZATION OF FATTY ACIDS

BACKGROUND OF THE INVENTION

1. Field of the Invention

The present invention relates to a procedure whereby fatty acids found in various oils, such as for instance, tall oil and soybean oil, are polymerized so as to obtain a mixture rich in dimeric and trimeric fatty acids. More particularly, it relates to a method for polymerizing unsaturated fatty acids, utilizing stepwise catalytic reactions.

2. Brief Description of the Prior Art

It is well known that monomeric unsaturated fatty acids which are derived from natural sources are capable of being polymerized to the dimerized and trimerized form. This is usually realized by heating such unsaturated fatty acids in the presence of catalytic proportions of a mineral clay and, preferably, an acid-treated mineral clay, at temperatures in excess of about 180° C. in an aqueous environment under autogenous pressure. Small amounts of water are deemed necessary for reaction to minimize the degradation of the fatty acids being treated. Representative of the prior art teachings are those found in the U.S. Pat. Nos. 2,793,219 and 2,793,220.

The U.S. Pat. No. 3,422,124 describes an improvement over the above-described prior art processes in that higher overall yields of the desired dimer and trimer products could be obtained by a two stage heating process. As explained in the U.S. Pat. No. 3,422,124, after a polymerization, which may yield around 60 percent polymeric species, the residual monomeric acids are unpolymerizable. However, the patentees discovered that if the initial polymerization were carried out under anhydrous conditions and in the presence of (a) glacial acetic acid, anhydrous propionic acid or anhydrous butyric acid, (b) an acid-treated mineral clay catalyst and (c) unsaturated fatty acids, then residual monomeric fatty acids could be polymerized in a second, conventional polymerization stage. This, of course, improved overall yields of dimer and trimer.

The two-stage polymerization was also used in the process disclosed in U.S. Pat. No. 3,632,822, which does not require the anhydrous and acid conditions recited in the U.S. Pat. No. 3,422,124. The patentee of the U.S. Pat. No. 3,632,822 revealed that those conditions were not required if one employed as the catalyst an acid-activated clay modified with an alkaline earth metal salt such as calcium chloride.

The process of the present invention is yet another improvement over the prior art processes. By the employment of an unactivated clay catalyst in a two-stage polymerization it has been found that still improved overall yields of dimer and trimer product may be achieved. The elimination of the need for an acid-activated clay catalyst has obvious advantages. Still further the dimer-trimer products have light colors and low viscosities, i.e., less than 10000 Cst @ 25° C. Other advantages of the process of the invention will be described hereinafter.

SUMMARY OF THE INVENTION

The invention comprises a method of polymerizing a mixture of polymerizable fatty acids, which comprises;

heating the mixture to a temperature of from 180° C. to 270° C. at a steam pressure of 50–180 psig in the presence of a catalytic proportion of an unactivated clay and a modifying proportion of an alkali or alkaline earth metal salt until about 40 percent to 60 percent by weight of the acids have polymerized; and separating from the polymerization mixture a monomer acid fraction and treating it with the catalyst system and conditions until there is essentially complete conversion of the oleic and elaidic acids.

This process is an improvement over the prior art in that high yields of light colored, low viscosity dimer are produced and acid activated clays, which are chemically and structurally modified natural clays, are not used.

BRIEF DESCRIPTION OF THE DRAWING

The accompanying drawing is a schematic flow chart showing a preferred embodiment process of the invention.

DETAILED DESCRIPTION OF THE PREFERRED EMBODIMENTS OF THE INVENTION

The method of the invention may be employed advantageously to polymerize a wide variety of fatty acids that are naturally occurring mixtures of monounsaturated and polyunsaturated fatty acids. Exemplary of monounsaturated acids are: oleic acid, elaidic acid and palmitoleic acid. Examples of polyunsaturated acids are: linoleic acid and linolenic acid. Mixtures of both monounsaturated acids and polyunsaturated acids are exemplified by tall oil fatty acids and soybean fatty acids, each of which contains less than about 10% conjugated unsaturation and having chain lengths of not less than 12 carbon atoms, usually between 16 and 22 carbon atoms.

Prior art, U.S. Pat. Nos. 3,422,124 and 3,632,822 indicate that acid-treated clays, i.e., clays that are structurally and chemically altered by treatment with strong inorganic acids, are necessary for high yields in a two-stage dimerization. My present invention is that certain natural clays, modified with alkaline and alkali earths, can be used to give not only high yields of dimer in a two-stage process, but that the dimer is also of light color and low viscosity.

The unactivated clay catalysts employed in the process of the invention are well known and commercially available. Representative of such clays are hectorite, montmorillonite, attapulgite, sepiolite, bentonite per se or in combination with montmorillonite. The clays are employed in catalytic proportions, generally within the range of from 1 to 10 percent by weight of fatty acid.

Advantageously employed in the method of the invention is a modifying proportion of a catalyst modifier, i.e., an alkali or alkaline earth metal salt. The modifier affects the selectivity of dimer in the reaction product. Additionally, when the modifier is lithium carbonate, lithium hydroxide or other lithium salts, the coloration of the product polymeric fatty acids is improved (reduced).

The proportion of lithium salt employed is generally within the range of from 0.5 to 6 meq per gram of clay catalyst employed.

Referring now to the accompanying drawing, a representative process of the invention will be described. As shown in the drawing, a suitable reactor vessel 1 is charged with a mixture of unsaturated fatty acids such as tall oil fatty acids and 1 to 10 percent by weight of an unactivated clay catalyst. A modifying proportion of an alkali or alkaline earth metal salt is also charged to vessel 1. The charge is heated to a temperature within the range of from 180° C. to 270° C. under a pressure of 50-180 psig. The pressure may be generated either by addition of water to the charge (0.5-10 percent by weight of tall oil fatty acids) or by addition of steam to the hot reaction mixture. The heating is continued until most of the linoleic acid and part of the oleic acid have polymerized and the yield of polymer is on the order of 40-60%, based on the weight of the fatty acid mixture charged. This usually requires a heating time within the range of about 1 to 5 hours; preferred conditions being about 2 hours at 255°-265° C. and 80-100 psig. The contents of the reactor vessel 1 are then discharged through a conduit line 2 into filter 3, through a conduit line 4 into a wiped film still 5 from which the unpolymerized acids are distilled through line 6 and are cooled and condensed into a receiver 7. A mixture of dimeric acids and trimeric acids, which ordinarily contains at least 75% of dimer acids, is withdrawn through conduit line 8 into a receiving tank 9.

The major proportion of the monomeric fatty acids collected in receiver 7 are polymerizable in character, being principally (45-60%) the straight-chain monounsaturated acids previously described, as well as 5-20% branched acids and 5-15% cyclic $C_{18}$ acids. This mixture is therefore charged into reactor 1 together with from 1% to 10% and preferably about 4% of fatty acid weight of an unactivated clay catalyst and a modifying proportion of an alkali or alkaline earth metal salt. The reaction mixture in reactor 1 is then heated to a temperature of between 180° C. to 270° C., preferably 255°-265° C. under pressures of 50-180 psig for from 2 to 5 hours. The steam pressure may be generated either by addition of water (0.5-10% by weight of fatty acids) to the charge or by addition of steam to the hot reaction mixture. At the end of this time period the reaction mixture is allowed to cool to ambient temperatures and is then withdrawn through conduit line 11 into filter 3, through conduit line 12 and separated in still 5. The separated dimer and trimer acids are carried through conduit line 15 to a storage vessel 16. The residue unpolymerizable monomer $C_{18}$ acids are removed through line 13 and condensed into a vessel 14.

In the first polymerization step the linoleic acid content of the tall oil fatty acid feed mixture is the most rapidly consumed reagent as the polymer acids are formed, for it is much more reactive than is the oleic acid component at the temperatures employed. This polymerization includes mainly the reaction between two molecules of linoleic acid, and in addition, reaction between one molecule of linoleic acid and one of oleic acid and between two molecules of oleic acid. The dimer acid product formed in the first stage is therefore more highly unsaturated than is that from the second stage.

After completing the first polymerization stage in the manner described, the reaction products are separated into a polymer fraction and a monomer fraction. This is preferably done by vacuum distillation, with or without the use of steam. The mixed reaction products are preferably fed into a wiped film still in which the monomer fraction is vaporized and separated as distillate while the polymer fraction is collected as a liquid from the base of the still. Distillation temperatures of 180° C.-275° C., at pressures of about 0.5-50 millimeters of mercury, are preferably maintained, but not especially critical.

The monomer fraction of the product mixture from the first stage consists principally (45-65%) of monounsaturated straight-chain fatty acids of 18 carbon atoms, mostly oleic and elaidic acids. Since these acids are polymerizable, they are advantageously subjected to the second polymerization stage. The second polymerization stage, like the first, is carried out in the presence of the catalyst modifier and about 1% to 10% by weight of fatty acid of the clay, the polymerization temperature being preferably the same as that used in the first stage and the steam pressure similar to that of the first stage. The material being polymerized in this second stage consists predominantly of oleic and elaidic acids, which require at least as high a temperature for polymerizing as does the mixture of oleic and linoleic acids which was the feed to the first stage. When these conditions are observed, and when the second stage polymerization is carried out for about 2 to 5 hours at steam pressures of 50-180 psig, yields of dimer acid are obtained in the 30 to 60 percent range or higher. Overall combined yields from both stages may be in the range of 65 to 75 percent, based on the feed material.

The following example describes the manner and process of making and using the invention and sets forth the best mode contemplated by the inventor for carrying out the invention.

EXAMPLE 1

Stage 1

Tall oil fatty acids (Unitol BKS*, Union Camp Corporation, Wayne, N.J.), 2% Montmorillonite Clay, 1.1 meq of lithium salt per gram of clay, and 5% water are stirred and heated in an autoclave at 260° C. and 90 psig for 1.75 hrs. The crude product mixture is cooled to 130° C. and treated with 1.1 wt. percent of 85% phosphoric acid at that temperature for 1 hr then filtered to remove the catalyst. The crude dimer typically has a Gardner color of 6+. A sample of the crude dimer is analyzed by high pressure liquid chromatography to determine monomer, dimer, and trimer content. Separation of the monomeric and polymeric acids by distillation at 225° C. and 0.7 mm shows that 49% polymeric acids and 51% unpolymerized material are present.

* Composition: 48.8% oleic acid, 34.3% linoleic acid, 6.4% conjugated linoleic acid, and 8.5% saturated $C_{12}$-$C_{20}$ acids.

The properties of the polymeric acids are shown in the TABLE 1, below. The monomer content is determined by gas chromatography of the methyl esters on an SP2330 column. The trimer content is determined by high pressure liquid chromatography on a 25 cm Zorbax column with an IR detector. The acid number is determined by ASTM D-1980 and the viscosity by ASTM D-446-74.

Stage 2

The monomeric acids from Stage 1 are heated in an autoclave with 4.3% Montmorillonite Clay, 1.1 meq of lithium salt per gram of clay, and 5% water at 260° C. and 90 psig for 3 hrs. The product is treated with 85% phosphoric acid, filtered, and separated via vacuum distillation to give an additional 41% of polymerized acids with the properties given in TABLE 1, below. The total yield of polymeric acids from the two stages is 70%.

TABLE 1

PROPERTIES OF POLYMERIC ACIDS FROM THE TWO STAGES

|  | Stage 1 | Stage 2 |
| --- | --- | --- |
| Acid No. | 190 | 192 |
| Viscosity Cst @ 25° C. | 7640 | 9660 |
| Monomer (%) | 0.3 | 0.1 |
| Trimer (%) | 11 | 8 |

EXAMPLE 2

Stage 1

Tall oil fatty acids (Unitol BKS), 4.3% Montmorillonite Clay, 4 meq of lithium salt per gram of clay, and 5% water are stirred and heated in an autoclave at 260° C. and 150 psig for 2 hrs. The crude product mixture is cooled to 130° C. and treated with 4.4% of 85% phosphoric acid at that temperature for 1 hr then filtered to remove the catalyst. Separation of the monomeric and polymeric acids by distillation at 225° C. and 0.7 mm gives 52% polymeric acids and 48% monomeric acids.

Stage 2

The monomeric acids are polymerized as described in Example 1. The yield of polymerized acids from the second polymerization is 43%. The total yield of polymeric acids from the two stages is 73%. The properties of the polymeric acids from the two stages are given in TABLE 2.

TABLE 2

PROPERTIES OF POLYMERIC ACIDS FROM THE TWO STAGES

|  | Stage 1 | Stage 2 |
| --- | --- | --- |
| Acid No. | 192 | 189 |
| Viscosity Cst @ 25° C. | 7670 | 8990 |
| Monomer (%) | 0.4 | 0.2 |
| Trimer (%) | 14 | 15 |

EXAMPLE 3

In a single stage process, tall oil fatty acids, 4.3% Montmorillonite Clay, 1.1 meq of lithium salt per gram of clay, and 5% water are stirred and heated in an autoclave at 260° C. and 90 psig for 2.5 hrs. The crude product mixture is treated with 1.1% of 85% phosphoric acid at 130° C. and then filtered to remove the catalyst. The yield of polymerized acids recovered after vacuum distillation is 63%.

What is claimed:

1. A method of polymerizing a mixture of polymerizable fatty acids, which comprises;

heating the mixture to a temperature of from 180° C. to 270° C. at a steam pressure of 50-180 psig in the presence of a catalytic proportion of an unactivated clay and a modifying proportion of lithium salt until about 40 percent to 60 percent by weight of the acids have polymerized; and separating from the polymerization mixture a monomer acid fraction and subjecting said fraction to the polymerization conditions above to give an additional yield of polymeric fatty acid.

2. The method of claim 1 wherein the mixture is composed mainly of monounsaturated and diunsaturated eighteen carbon fatty acids.

3. The method of claim 1 wherein the mixture is tall oil fatty acids.

4. The method of claim 1 wherein the mixture is soybean fatty acids.

5. The method of claim 1 wherein the unactivated clay is montmorillonite.

6. The method of claim 1 wherein the weight of unactivated clay is 1-10% of the weight of the fatty acids.

7. The method of claim 1 wherein the modifying alkali or alkaline earth metal salt is lithium carbonate.

8. The method of claim 1 wherein the modifying alkali or alkaline earth metal salt is lithium hydroxide.

9. The method of claim 1 wherein the reaction temperature for both stages is 250°-265° C.

10. The method of claim 1 wherein the reactor steam pressure is 80-100 psig.

* * * * *